United States Patent [19]

Phan et al.

[11] Patent Number: 5,192,286
[45] Date of Patent: Mar. 9, 1993

[54] METHOD AND DEVICE FOR RETRIEVING MATERIALS FROM BODY LUMENS

[75] Inventors: Cu N. Phan; Marshall L. Stoller, both of San Francisco, Calif.

[73] Assignee: Regents of the University of California, Oakland, Calif.

[21] Appl. No.: 736,173

[22] Filed: Jul. 26, 1991

[51] Int. Cl.⁵ .............................................. A61M 25/00
[52] U.S. Cl. .................................. 606/127; 604/264; 604/265; 606/1; 606/106; 606/110; 606/113; 606/114
[58] Field of Search ............... 606/106, 110, 113, 114, 606/127, 128, 159, 194; 604/264, 265, 280, 281

[56] References Cited

U.S. PATENT DOCUMENTS

| | | | |
|---|---|---|---|
| 156,477 | 11/1874 | Bradford | 606/127 |
| 460,940 | 10/1891 | Baugh | 606/106 |
| 1,677,671 | 7/1928 | Councill | 606/127 |
| 2,918,919 | 12/1959 | Wallace | 606/127 |
| 3,008,467 | 11/1961 | Morris | 606/127 |
| 3,108,593 | 10/1963 | Glassman | 606/127 |
| 3,108,594 | 10/1963 | Glassman | 606/127 |
| 3,472,230 | 10/1969 | Fogarty | 606/127 |
| 3,566,874 | 3/1971 | Shepherd | 604/265 |
| 3,726,281 | 4/1973 | Norton | 604/265 |
| 3,908,661 | 9/1975 | Kramer | 606/127 |
| 4,030,503 | 6/1977 | Clark, III | |
| 4,046,149 | 9/1977 | Komiya | 606/127 |
| 4,650,466 | 3/1987 | Luther | |
| 4,706,671 | 11/1987 | Weinrib | |
| 4,807,626 | 2/1989 | McGirr | 606/127 |
| 4,873,978 | 10/1989 | Ginsburg | |
| 4,893,621 | 1/1990 | Heyman | |
| 5,013,310 | 5/1991 | Goode | |
| 5,108,406 | 4/1992 | Lee | 606/106 |
| 5,122,147 | 6/1992 | Sewell | 606/113 |
| 5,147,371 | 9/1992 | Washington | 606/113 |

FOREIGN PATENT DOCUMENTS

| | | | |
|---|---|---|---|
| 0025796 | 1/1884 | Brazil | 606/127 |
| 2821048 | 11/1979 | Fed. Rep. of Germany | 606/106 |
| 3522649 | 1/1986 | Fed. Rep. of Germany | 606/127 |
| 3913935A1 | 10/1990 | Fed. Rep. of Germany | |
| 3913936A1 | 10/1990 | Fed. Rep. of Germany | |

OTHER PUBLICATIONS

Mauermayer, *Transurethral Surgery*, 1983, pp. 370–374, Springer-Verlag, Berlin Heidelberg, New York.
Huffman, Bagley & Lyon, *Uretheroscopy*, 1988, pp. 88–92, W. B. Saunders Company.

*Primary Examiner*—Stephen C. Pellegrino
*Assistant Examiner*—Glenn Dawson
*Attorney, Agent, or Firm*—Townsend and Townsend

[57] ABSTRACT

A retrieval catheter (10) for removing deleterious materials (S) from body lumens has an elongate catheter body (12) having a slack net (26) at its distal end (16). The slack net may be collapsed to facilitate introduction into the body lumen and opened in situ to permit capture and retrieval of the deleterious materials. A method for removing ureteral stones from the ureter is described.

26 Claims, 4 Drawing Sheets

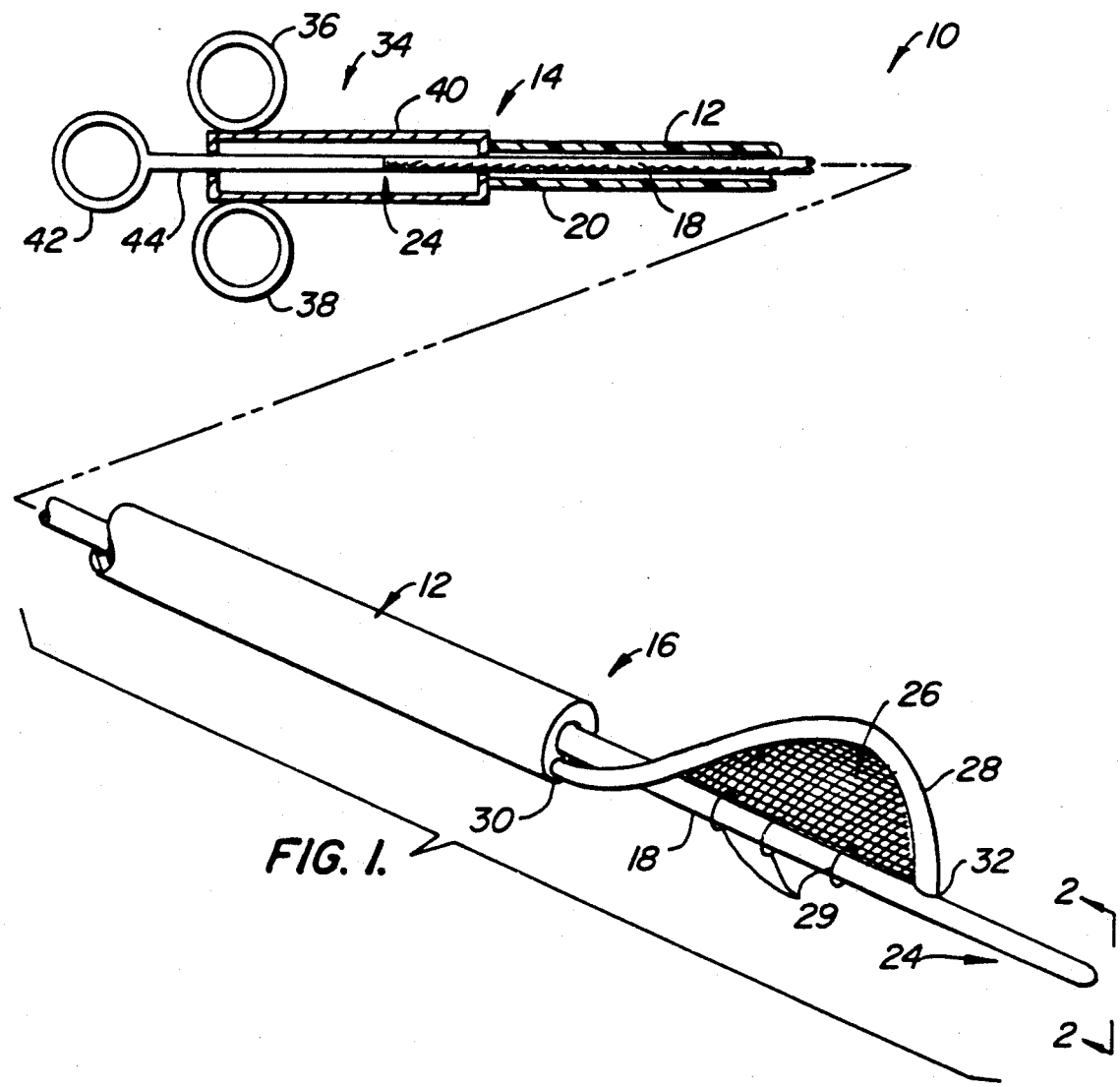
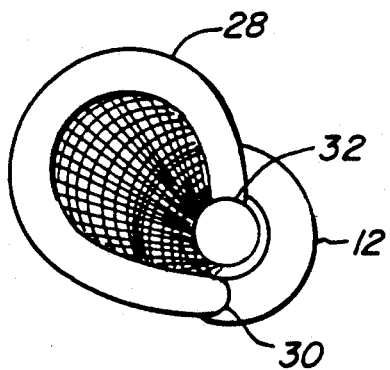
FIG. 2.
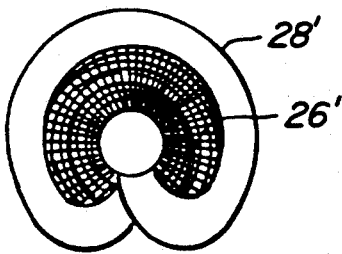
FIG. 2A.

METHOD AND DEVICE FOR RETRIEVING MATERIALS FROM BODY LUMENS

BACKGROUND OF THE INVENTION

1. Field of the Invention

The present invention relates generally to the construction and use of medical instruments for retrieving deleterious materials from body lumens. More particularly, the present invention relates to a catheter having a slack capture net at its distal end and means at its proximal end for opening and closing the net to capture and retrieve materials from body lumens.

The retrieval of ureteral stones remains a challenge and an occasional frustration to the treating surgeon. While blind retrieval techniques have been replaced by methods which employ direct visualization using a variety of endoscopes, stone retrieval can still be troublesome because of inadequacies in the retrieval device employed.

Conventional ureteral stone retrieval devices fall into several categories, including baskets, pincer-like forceps, graspers, and slings. Basket retrieval devices generally employ collapsible wire prong structures having relatively large openings which allow passage of small stones and stone fragments. The capture of large stones can also be difficult since the stone will frequently hinder movement of the basket in order to engage the stone. Such baskets also have a tendency to lose the stones as the basket is being withdrawn from the ureter.

The use of pincer-like forceps, graspers, and slings, is similarly problematic. Such devices usually can capture only one stone at a time. Frequently, vision through the ureteroscope is sufficiently poor to render capture of single stones difficult.

For the reasons, it would be desirable to provide improved devices and methods for capturing ureteral stones during stone removal procedures. It would be particularly desirable if the device could be used for other medical procedures, including the removal of biliary stones from the biliary tract, the removal of atheroma and plaque from the vascular system, and the like.

2. Description of the Background Art

U.S. Pat. No. 4,706,671, describes an atheroma removal catheter having an expandable helical coil at its distal end. U.S. Pat. No. 4,650,466, describes an angioplasty catheter having an expandable woven tube and optional internal filter for collecting plaque dislodged from a blood vessel by the tube. U.S. Pat. No. 4,873,978, describes an expandable strainer which may be introduced downstream of an angioplasty procedure to capture released emboli. U.S. Pat. 4,030,503, describes an embolectomy catheter having a helical wire structure at its distal end.

SUMMARY OF THE INVENTION

The present invention provides improved devices and methods for the retrieval of material from body lumens. The device is a retrieval catheter which comprises a catheter body having a slack net at its distal end. The catheter further includes means at the proximal end of the catheter body for opening and closing or "collapsing" the slack net so that the catheter can be introduced into a body lumen with the net in its collapsed configuration, and the net then opened after it reaches a desired location. The slack net comprises a permeable fabric, which may be elastic or not but is preferably a slightly elastic nylon or other fabric, so that it permits fluid flow therethrough by remaining able to capture both large and small particles, stones, stone fragments, and the like, with the capability of capturing many pieces at a time. A somewhat elastic fabric is particularly suitable since it can accommodate a large volume of material and will secure the captured material tightly to reduce the likelihood that the material will be lost while the catheter is being withdrawn from the body lumen.

In a preferred embodiment, the slack net is mounted on a flexible loop which acts as an expandable frame for holding the net. Usually, the flexible loop will have two ends, one of which is attached near the distal end of the catheter body and the other which is attached to a flexible core, such as a solid flexible pull-wire or a flexible cylindrical tube, which extends through a central lumen of the catheter body. In this way, the loop can be straightened so that it assumes a collapsed configuration, i.e., lying next to the distally extended pull-wire. By axially translating (pulling) the pull-wire in the proximal direction, however, the flexible loop will reassume a generally circular shape so that the slack net is opened and disposed to receive the material which is to be retrieved. Preferably, the flexible loop will be coated with or formed from a lubricous material, more preferably being coated with a hydrophilic material to facilitate introduction and manipulation of the catheter to and within the body lumen.

In the most preferred embodiment, the loop will be wrapped around the catheter body from one-half turn (180°) to one full turn (360°). In this way, the slack net will be wound partly or fully around the catheter body when the flexible loop is in its collapsed configuration. Similarly, the net will extend partly or fully around the catheter body when the flexible loop is in its open configuration.

In the method of the present invention, the catheter body is introduced to the desired body lumen, such as the ureter, biliary duct, blood vessel, bronchus, esophagus, bladder or the like, with the slack net in its collapsed configuration. Usually, the catheter will be introduced while being visualized by a conventional technique, such as ureteroscopy, fluoroscopy, or the like. Once in place, the slack net can be opened to extend across a major portion of the body lumen so that it can capture solid material which may be present. The permeable nature of the slack net, permits the flow of body fluids, such as urine, bile, blood, and the like therethrough. The solid material, such as ureteral and biliary stones, foreign bodies or other deleterious material may be captured by axially translating the catheter within the lumen so that the net engages the material. Alternatively, the net can be left stationary to capture material which is carried by flowing body fluid, e.g., emboli carried by the blood. In either case, after the material is captured, the net can be collapsed to secure the material, and the catheter then withdrawn from the body lumen.

The invention can also be practiced without the slack net. According to this aspect of the invention, the catheter acts as an endoscopic retractor to enlarge a body cavity to facilitate medical procedures at the site of the flexible loop. For example, the distal end of the endoscopic retractor could be positioned along a body lumen adjacent a stone. When properly positioned adjacent a stone, the pull wire is pulled to expand the flexible loop, thus opening the body lumen adjacent the stone. This provides other endoscopic devices, such as ultrasonic or laser probes, clear access to the stone to break up the stone.

BRIEF DESCRIPTION OF THE DRAWINGS

FIG. 1 is a perspective view of a retrieval catheter constructed in accordance with the principles of the present invention, shown with the proximal end in section.

FIG. 2 is a front end view of the retrieval catheter of FIG. 1, taken from line 2—2.

FIG. 2A illustrates an alternative embodiment of the distal end of the retrieval catheter of FIG. 1.

DESCRIPTION OF THE SPECIFIC EMBODIMENTS

Figure 3A:
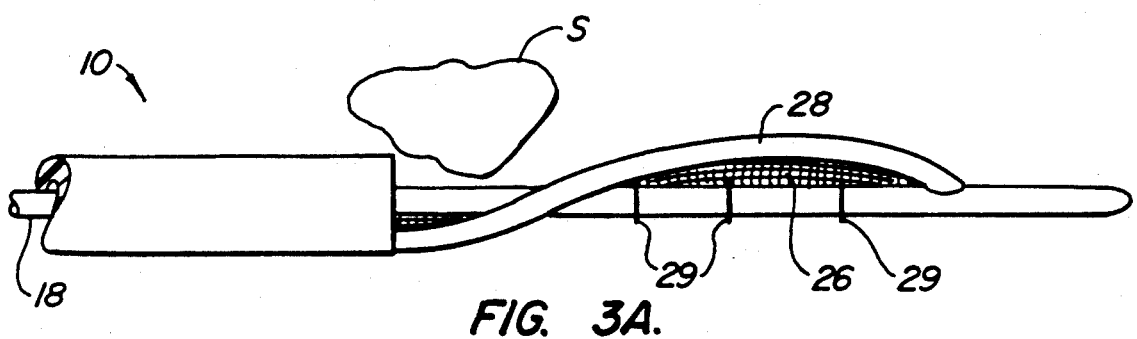
FIGS. 3A-3C illustrate use of the retrieval catheter of FIG. 1 in retrieving a ureter stone from the ureter.

The present invention is useful for capturing and retrieving potentially harmful materials from body lumens, such as ureteral stones from the ureter, biliary stones from the biliary duct, atheroma and plaque from blood vessels, and the like. The device of the present invention is a retrieval catheter which comprises an elongate body having proximal and distal ends and a slack net at or near the distal end of the elongate body for capturing and retrieving the materials. The device further includes means for opening and collapsing the slack net while the catheter is in situ within the desired body lumen. In this way, the catheter can be introduced with the slack net collapsed so that the catheter has a minimum cross-sectional area to facilitate introduction and placement. The slack net can then be opened to permit capture of the body lumen materials, as described in more detail hereinbelow in connection with the method of the present invention.

The catheter body may be flexible or rigid, although flexible catheters are preferred for most applications. The length of the catheter body will vary depending on the application, with short catheters having a length in the range from about 40 cm to 100 cm, being preferred for stone removal applications from the ureter, biliary duct, and the like. Longer catheters having a length from 50 cm to 150 cm will be preferred for most vascular applications. The diameter of the catheter body will also depend on the application. For use in the ureter and biliary duct, the catheter will usually have a diameter in the range from about 4 French to 12 French, usually being in the range from 5 French to 8 French. For vascular applications, the diameter will usually be in the range from 6 French to 10 French.

Flexible catheter bodies will typically be formed as hollow tubes from extruded organic polymers, such as silicone rubber, polyurethane, polyvinyl chloride, nylon, and the like. In some cases, it may be desirable to reinforce such polymeric catheter bodies, typically using a braided or other flexible reinforcement layer. Suitable materials and construction techniques for preparing tubular catheter constructions are well described in the medical and scientific literature and need not be described in detail herein.

The slack net of the present invention will be permeable or porous to permit the flow of body fluids therethrough, but will define sufficiently narrow passages so that even very small stone fragments or other materials to be captured will be unable to pass therethrough. Conveniently, the slack net will be formed from a woven or non-woven fabric, or the like, where the interstices between the fibers which form the fabric permit capture of the stone material while allowing flow of the body fluid therethrough. Such fabrics will be composed of a biocompatible material, typically being formed from a natural fiber or an organic polymer, preferably being formed from organic polymers. Thin metallic threads may also be used. Suitable organic polymers include nylon, polyethylene, polypropylene, polyester, polytetrafluorethylene (PTFE), polycarbonate, polystyrene, cellulose, polyacetonitrile, and the like. Individual fibers or bundles of fibers (yarns) may be woven into the fabric by conventional techniques, such as weaving, braiding, knitting, and the like. The porosity of woven fabrics will be determined primarily by the interstitial spaces between the woven fibers or yarns, with looser weaves providing lesser flow resistance.

Particularly preferred for the present invention are fabric materials formed from threads which are thin and strong to form a fabric which is elastic or not. The fabric materials are preferably slightly elastic, such as elastic woven nylons of the type employed in conventional hosiery.

Referring now to the drawings, a preferred catheter construction for mounting a slack net at the distal end of an elongate catheter body will be described. A retrieval catheter 10 comprises an elongate body 12 having a proximal end 14 and a distal end 16. A pull wire 18 extends through the axial lumen 20 of the catheter body 12 and includes a proximal end 24 and a distal end 22. The pull wire 18 may be formed from any material having sufficient compressive strength and bending stiffness so that it can be used to manipulate slack net structure 26 mounted near its distal end. Usually, the pull wire will be a hollow tube or a solid core wire, a twisted strand wire, a braided wire, or the like. Particularly suitable materials and constructions of the type used in the construction of conventional guide wires.

The slack net structure 26 is secured to a flexible loop member 28, which in turn is secured at a first end 30 to the elongate body 12 and at a second end 32 to the pull wire 18. The slack net 26 is attached along substantially the entire length of the flexible loop member 28 so that the position and configuration of the loop member will necessarily define the outer periphery of the slack net.

The slack net may or may not be secured to the pull wire. If secured, the means for securing must be able to translate along the pull wire 18 as it is moved in and out of lumen 20 of the catheter body. For example, the slack net can be slidably secured with a plurality of rings 29 which slide along the pull wire 18 as the net is opened and closed.

The pull wire 18 can be axially translated within the lumen 20 of catheter body 12 using a conventional three-ring actuator assembly 34 attached to the proximal end 14 of catheter body 12. The three-ring actuator assembly 34 includes a pair of side rings 36 and 38 attached to a central housing 40. A thumb ring 42 is secured to a plunger rod 44 which extends into the interior of the housing 40 and is secured to the proximal end of the pull wire 18. In this way, the treating physician can manipulate the position of the distal end of pull wire 18 relative to the distal end of catheter body 12 using a single hand.

It will be appreciated that the flexible loop member 28 can be "opened" and "collapsed" relative to the catheter body 12 and pull wire 18 by axially advancing or retracting the pull wire. That is, by fully extending the pull wire 18 in the distal direction, the flexible loop member 28 will be collapsed so that it lies adjacent the pull wire 18 (as best observed in FIG. 3A), thus closing the slack net structure 26. Conversely, by fully retracting the pull wire 18 relative to the catheter body 12 (as best observed in FIG. 3C), the loop member 28 will be fully opened as will be the slack net structure 26.

Referring now to FIGS. 2 and 2A, it can be seen that the attachment of flexible loop member 28 to the catheter 10 can be varied in order to change the geometry of the slack net structure 26 when it is fully opened. In FIG. 2, the flexible member 28 is oriented substantially as illustrated in FIG. 1. The distal end 30 of the flexible loop member 28 is attached at the six o'clock position on the catheter body 12, while the distal attachment point 32 is attached at the 12 o'clock position on the pull wire 18. Thus, when the pull wire 18 is fully retracted and the loop 28 fully opened, the loop will be primarily on one side of the elongate body 12. This is generally a preferred configuration.

An alternative configuration is illustrated in FIG. 2A, where flexible member 28' is wrapped around the pull wire one complete revolution (360°) so that the loop and net 26' will open up substantially symmetrically about the catheter when opened.

The flexible loop member 28 will preferably be formed from a resilient material possessing a memory so that, when the pull wire 18 is retracted, the loop will regain a preset circular configuration. Suitable memory materials include metals, flexible plastics, and the like.

Preferably, the flexible loop 28 will be coated with a lubricous material to facilitate introduction and manipulation within the desired body lumen. More preferably, the loop member will be coated with a hydrophilic material. Such lubricous and/or hydrophilic materials are particularly desirable since they permit the distal end of the catheter 10 to be axially advanced and manipulated within the body lumen with minimal friction and binding For example, such lubricous and/or hydrophilic loop members will permit the loop 28 and slack net structure 26 to be passed around even relatively large stones in the ureter or biliary duct to permit capture and retrieval of such stones.

Preferred materials for coating the flexible member 28 include that used on the Terumo Glide Wire made by Microvasive of Boston, Mass.

Figure 3B:
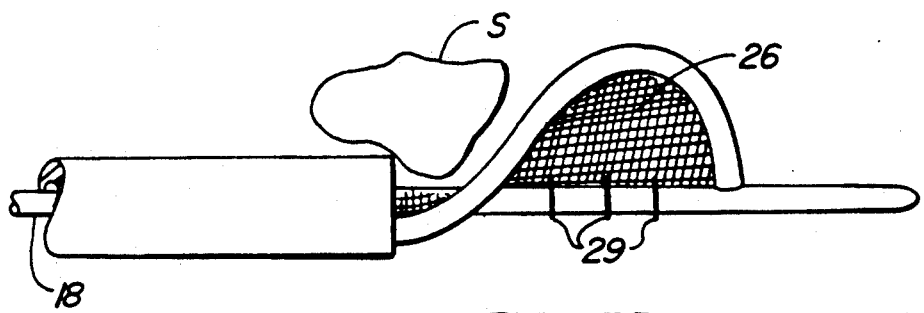
Figure 3C:
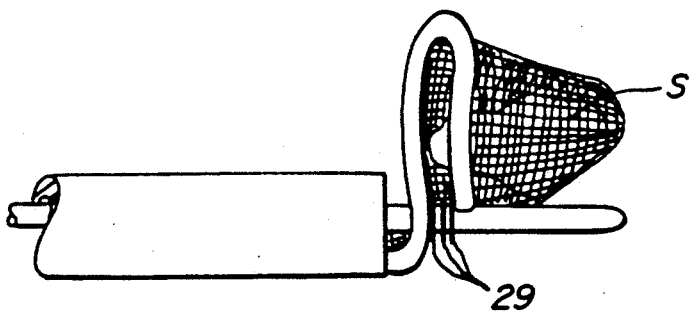

Referring now to FIGS. 3A-3C, the method of the present invention used for removing a ureteral stone S will be described. The catheter 10 is introduced to the ureter in a conventional manner, such as through a cystoscope or a ureterescope or over a guide wire.

Catheter 10 is inserted with the flexible loop member 28 fully collapsed, as shown in FIG. 3A. The catheter is advanced until the ureteral stone S lies next to the flexible loop member 28 and slack net structure 26. The net 26 can then be opened by retracting pull wire 18 using the three-ring assembly 34. The net structure 26 is shown in a partly opened configuration in FIG. 3B and in a fully opened configuration in FIG. 3C. After the net structure 26 is fully opened, the ureteral stone S may be captured simply by drawing the catheter 10 in the proximal direction so that the stone S falls into the slack net.

The stone S may then be secured within the net 26 by forwardly advancing the pull wire 18 to collapse the net around the stone (not illustrated).

Catheter 10 may be advanced over a guide wire as is routine in radiological or vascular procedures.

Figure 4A:
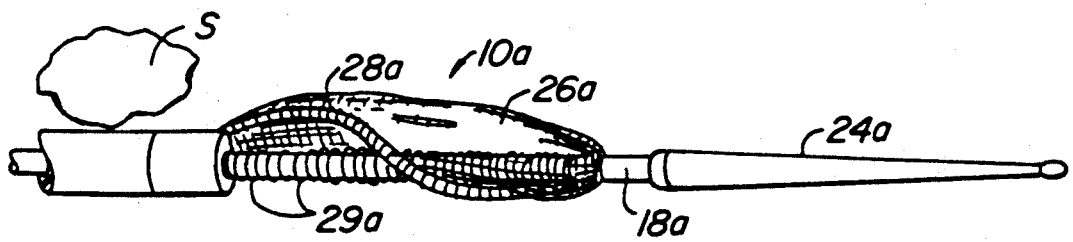
FIGS. 4A-4D illustrate use of an alternative embodiment of the retrieval catheter of FIG. 1 using a net which is less elastic than that of FIG. 1.
Figure 4B:
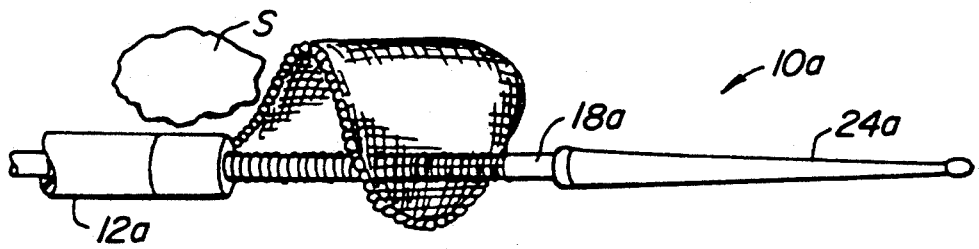
Figure 4C:
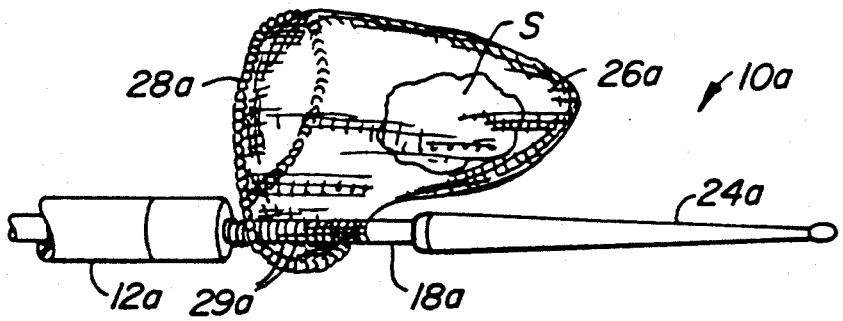
Figure 4D:
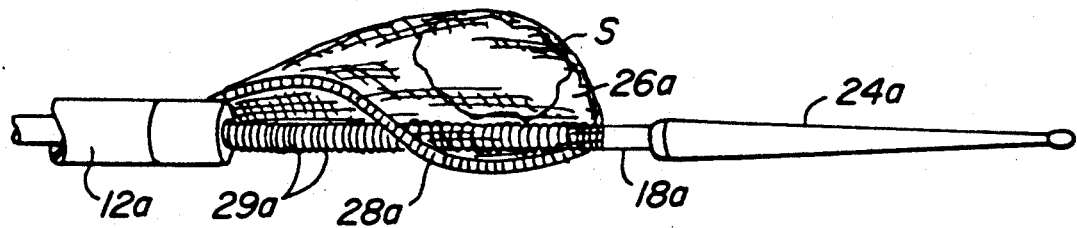

FIGS. 4A-4D illustrate an alternative embodiment of catheter 10 shown in FIG. 1-3C with like elements referred to with corresponding members. The primary difference between catheters 10 and 10a is the use of a nonelastic slack net 26a versus the slightly elastic net 26 of FIG. 1. FIG. 4A illustrates distal end of 24a before pull wire 18a has been pulled or retracted. FIG. 4B illustrates catheter 10a with pull wire 18a partially retracted as body 12a has been pulled back slightly towards stone S. FIG. 4C illustrates catheter 10a with pull wire 18a substantially retracted into body 12a having captured stone S within net 26a. FIG. 4D illustrates the structure of FIG. 4C after pull wire 18a has been extended back to the general position of FIG. 4A, thus capturing stone S within net 26a for withdrawal of the stone from the body lumen or cavity.

Figure 5A:
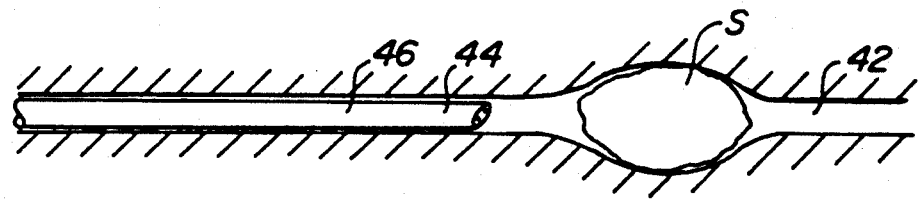
FIG. 5A illustrates a body lumen having a stone therein and showing the distal end of an endoscopic probe adjacent the stone.
Figure 5B:
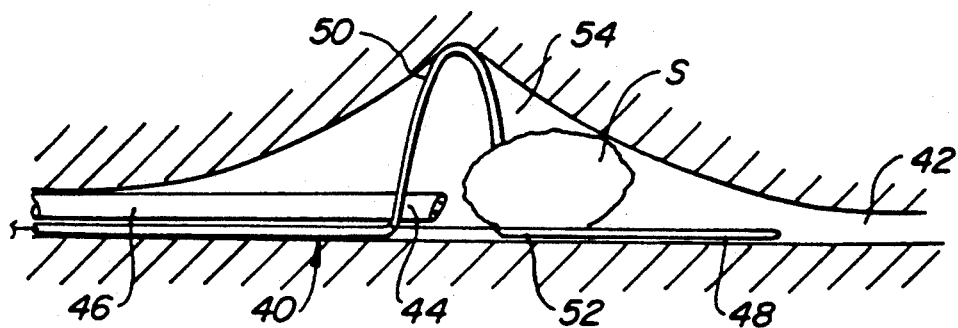
FIG. 5B illustrates the body lumen, stone and endoscopic probe of FIG. 5A with the flexible loop member of an endoscopic retractor positioned between the distal end of the endoscopic probe and the stone, the endoscopic retractor being similar to that shown in FIGS. 3C and 4C but without a net.

Retrieval catheter 10 can be modified through the removal of slack net structure 26 to create an endoscopic retractor 40 as shown in FIG. 5B. FIG. 5A illustrates a body lumen 42 having a stone S positioned along the body lumen. The distal end 44 of an endoscopic probe 46 is positioned along body lumen 42 adjacent stone S. The distal end 48 of endoscopic retractor 40 is then passed through body lumen 42 until flexible loop 50, similar to flexible loop member 28, is positioned between distal end 44 and stone S. Pull wire 52 is pulled to cause flexible loop 50 to assume its radially extended position of FIG. 5B to create an enlarged viewing region 54 surrounding loop 50. As is evident from FIG. 5B, this provides an enlarged region for the manipulation of distal end 44 of endoscopic probe 46. When endoscopic probe 46 is of an ultrasonic or laser probe used to break stone S into small bits, this can be accomplished much easier with retractor 40.

Figure 6A:
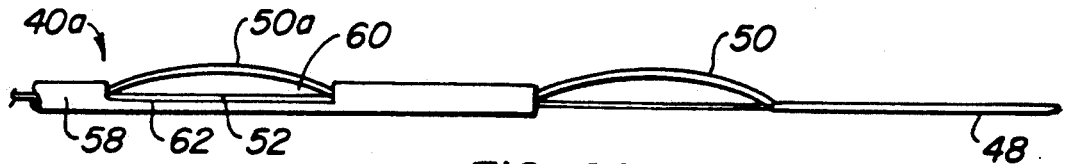
FIG. 6A shows an alternative embodiment of the endoscopic retractor of FIG. 5B having a pair of flexible loops.
Figure 6B:
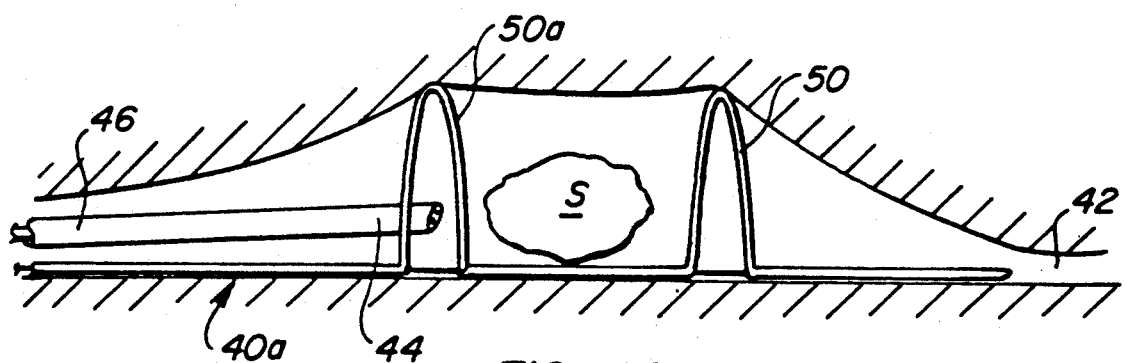
FIG. 6B shows the endoscopic retractor of FIG. 6A in a use situation similar to that of FIG. 5B with the flexible loops in their radially extended conditions on either side of the stone.

FIG. 6A illustrates an alternative embodiment of endoscopic retractor 40 by which a pair of axially separated flexible loops 50, 50a are used. The structure at loop 50 is substantially the same as the structure in the embodiment of FIG. 5B. However, body 58 includes a body extension 60 which is used to connect but separate the opposed ends of loops 50, 50a. Flexible loop 50a is secured at one end to body extension 60 and at the other end to body 58 while loop 50 is connected to pull wire 52 at one end and to body extension 60 at the other end. The use of endoscopic retractor 40a, by which flexible loops 50, 50a are positioned on either side of stone S, is shown in FIG. 6B.

Although the foregoing invention has been described in detail for purposes of clarity of understanding, it will be obvious that certain modifications may be practiced within the scope of the appended claims. For example, an additional tubular body could be mounted over body 12 so to slide over net structure 26 when in the collapsed position of FIG. 3A to aid insertion of catheter 10 into the body lumen. Once in position, the additional tubular body can be pulled back to expose net structure 26.

What is claimed is:

1. A retrieval catheter comprising:
   a hollow elongate body having proximal and distal ends;
   a flexible loop member, having first and second securing ends, secured to the distal end of the body by the first securing end;
   a slack net secured within the flexible loop; and
   means for opening and collapsing the loop, whereby the slack net can be opened in order to capture material and closed in order to secure the captured material.

2. A retrieval catheter as in claim 1, wherein the means for opening and collapsing the loop comprises means attached to the second securing end of the loop member for drawing the first and second securing ends together to open the net.

3. A retrieval catheter as in claim 2, wherein the means for drawing the two ends of the loop together comprises a pull wire which is slidably mounted within the elongate body.

4. A retrieval catheter as in claim 1, wherein the slack net comprises a permeable fabric.

5. A retrieval catheter as in claim 4, wherein the slack net comprises an elastic nylon fabric.

6. A retrieval catheter as in claim 1 wherein the second securing end of the loop member is attached to the means for opening and collapsing the loop.

7. A retrieval catheter comprising:
   an elongate body having proximal and distal ends;
   a pull wire having proximal and distal ends and being slidably mounted within the elongate body, wherein the distal end of the pull wire extends distally of the distal end of the said body;
   a flexible loop member, having first and second securing ends, wherein the first securing end is attached to the distal end of the elongate body and the second securing end is attached to the pull wire near the distal end of said pull wire; and
   a slack net attached to the flexible loop, whereby the net can be shifted between an open and a closed configuration by axially shifting the pull wire relative to the elongate body.

8. A retrieval catheter as in claim 7, further comprising means at the proximal end of the elongate body for axially shifting the pull wire relative to the elongate body.

9. A retrieval catheter as in claim 8, wherein the axially shifting means is a three-ring actuator.

10. A retrieval catheter as in claim 7, wherein the elongate body is a flexible tube having a central lumen which receives the pull wire.

11. A retrieval catheter as in claim 7, wherein the pull wire is one of a hollow tube, a solid core wire, a twisted strand wire, or a braided wire.

12. A retrieval catheter as in claim 7, wherein the flexible loop member has a lubricous outer surface.

13. A retrieval catheter as in claim 12, wherein the flexible loop has a hydrophilic outer surface.

14. A retrieval catheter as in claim 7, wherein the slack net comprises a permeable material.

15. A retrieval catheter as in claim 14, wherein the slack net comprises an elastic nylon fabric.

16. A retrieval catheter as in claim 14, wherein the slack net comprises material coated with a hydrophilic material.

17. A retrieval catheter as in claim 16, where the slack net comprises an elastic nylon fabric.

18. A retrieval catheter as in claim 14, wherein the slack net comprises a material made from thin metallic threads.

19. A method for retrieving material in a body lumen, said method comprising:
   introducing a hollow catheter body to the lumen, said catheter body having a collapsed slack net attached to a loop having two ends, one end being secured to a distal end of the catheter body;
   moving the collapsed slack net past the material;
   opening the slack net so that said net will extend across a portion of the cross section of the body lumen greater than a cross section of the catheter;
   manipulating the slack net and optionally the catheter body;
   capturing material within the opened slack net;
   collapsing the slack net on the captured material; and
   withdrawing the catheter body from the lumen.

20. A method as in claim 19, wherein the body lumen is the ureter and the material captured is ureteral stones or other deleterious material.

21. A method as in claim 19, wherein the body lumen is the biliary tract and the material captured is biliary stones or other deleterious material.

22. A method as in claim 19, wherein the body lumen is a blood vessel and the material removed is atheroma or blood clot or emboli.

23. A method as in claim 19, wherein the body lumen is a bronchus and the material is a foreign body or other deleterious material.

24. A method as in claim 19, wherein the body lumen is an esophagus and the material is a foreign body or other deleterious material.

25. A method as in claim 19, wherein the body lumen is a bladder and the material is a stone or other deleterious material.

26. A method as in claim 19, further comprising the step of using an additional endoscopic device to break up the captured material within the slack net before withdrawing the catheter body.

* * * * *